United States Patent
Williams

(10) Patent No.: US 6,706,840 B1
(45) Date of Patent: Mar. 16, 2004

(54) METHOD FOR PREPARING OXIRANE-CONTAINING ORGANOSILICON COMPOSITIONS

(75) Inventor: Darryl Stephen Williams, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/265,421

(22) Filed: Oct. 7, 2002

(51) Int. Cl.$^7$ ............................................. C08G 77/08
(52) U.S. Cl. ........................... 528/15; 528/27; 528/31
(58) Field of Search ........................... 528/15; 502/154

(56) References Cited

U.S. PATENT DOCUMENTS

| | | | | |
|---|---|---|---|---|
| 3,652,615 A | * | 3/1972 | Parasko | 528/15 |
| 4,511,715 A | * | 4/1985 | Palensky et al. | 528/15 |
| 4,966,981 A | * | 10/1990 | Takai et al. | 549/215 |
| 5,258,480 A | | 11/1993 | Eckberg et al. | |
| 5,391,676 A | | 2/1995 | Eckberg et al. | |
| 6,124,418 A | | 9/2000 | Crivello et al. | |
| 6,177,585 B1 | * | 1/2001 | Chen et al. | 556/479 |

OTHER PUBLICATIONS

Crivello, James V.; Fan, Mingxin, "Regioselective Ring-Opening Polymerizations and Hydrosilylations Catalyzed by Transition Metal Complexes", Polymer Preprints, Division of Polymer Chemistry, American Chemical Society v 32 n 1. Publ by ACS, Books & Journals.

J. L. Speier, "Homogeneous Catalysis of Hydrosilation by Transition Metals", in Advances in Organometallic Chemistry, vol. 17, pp. 407–447 (1979), F. G. A. Stone and R. West, eds., Academic Press (New York, San Francisco, London).

Crivello and Lee, "The Synthesis, Characterization, and Photoinitiated Cationic Polymerization of Silicon–Containing Epoxy Resins", J. Polymer Sci., vol. 28, John Wiley, New York 1990, pp. 479–503.

de Charentenay, F., Osborn, J. A., and Wilkinson, G., "Interaction of Silanes with Tris(triphenylphosphine)chlorohodium(1) and Other Rhodium Complexes; Hydrosilation of Hex–1–ene by Use of Trichlorosilane", J. Chem. Soc. A. 1968, p. 787.

Crivello, James V.; Fan, Mingxin, "Simultaneous Hydrosilation and Ring–Opening Polymerization as a Route to Novel Polymer Architectures", Macromol. Symp. 77, 413–421 (1994).

* cited by examiner

Primary Examiner—Margaret G. Moore
(74) Attorney, Agent, or Firm—Andrew J. Caruso; Patrick K. Patnode

(57) ABSTRACT

A method for preparing an organosilicon composition from an olefin and a silicon hydride with a hydrosilation catalyst $PtL_2X_2$, in an amount less than 1 ppm based on the weight of the product composition, is disclosed. The method is particularly useful in lowering the cost, coloration, and stability of the product, particularly when an oxirane-containing olefin is used in the hydrosilation. In this method no inhibitor is needed to prevent the undesired polymerization of oxiranes in the reaction, and no purification of the product is required after removal of volatile components, including solvent.

28 Claims, No Drawings

METHOD FOR PREPARING OXIRANE-CONTAINING ORGANOSILICON COMPOSITIONS

This invention was made with Government support under contract number 70NANB8H4022, awarded by NIST. The Government has certain rights in the invention.

BACKGROUND

The invention relates generally to a rapid, direct process for producing pure organosilicon compositions by hydrosilation of olefins and oxirane-containing olefins with silicon hydride groups by using extremely low levels of a platinum catalyst. Generally, hydrosilation catalysts are complexes of platinum, palladium, rhodium, iridium, iron or cobalt. Many of these transition metal hydrosilation catalysts also promote ring-opening polymerization of oxiranes in the presence of silicon hydrides. In this invention the hydrosilation reaction proceeds such that any oxirane rings in both the olefin and organosilicon product remain intact. Furthermore, the invention also relates to curable oxirane-containing siloxane (epoxysiloxane) compositions made by the above method. The ring-opening polymerization reaction during production of an oxirane-containing organosilicon composition may be undesirable as the oxirane polymerization may cause the reaction mixture to gel partially or completely, resulting in the loss of the entire batch and in loss of considerable time in cleanup of the insoluble gelled resin. Partial gelation due to the ring-opening polymerization reaction can occur during hydrosilations such that reproducible batch-to-batch viscosity of the oxirane-containing organosilicon product is difficult to obtain. Such reproducibility in viscosity is highly preferred in commercial applications of oxirane-containing organosilicon compositions and these materials may be used in applications such as coatings, and encapsulents and lens material for high luminosity light emitting diodes.

In some instances product oxirane-containing organosilicon compositions have been found to slowly gel on storage at room temperature in the presence of precious metal hydrosilation catalysts due to the oxirane ring-opening polymerization reaction, thus shortening the product shelf life. While this storage problem can be partially alleviated by deactivating the transition-metal-complex catalyst with an inhibitor, such as dodecyl mercaptan or 2-mercaptobenzothiazole in the case of platinum complexes, it would be preferable to not incorporate this extra component and additional process step into the process of producing the oxirane-containing organosilicon compositions. This storage problem can also be alleviated by ensuring complete consumption of the silicon hydride during the preparative process.

In general, careful control of batch temperature and oxirane-containing olefin feed rate during the synthesis, followed by the above-mentioned inactivation of the catalyst after the completion of the hydrosilation reaction is required in order to minimize the oxirane ring-opening polymerization reaction.

Certain hydrosilation catalysts containing phosphine ligands are known. For example, $RhCl(PPh_3)_3$ (Wilkinson's catalyst) efficiently catalyzes the hydrosilation reaction between SiH-containing silanes and siloxanes and vinyl oxiranes. Other rhodium-based catalysts have been reported to selectively promote the hydrosilation reaction without the promotion of an oxirane ring-opening polymerization reaction. A variety of epoxy-functionalized silicone monomers and oligomers have been synthesized using these catalysts. However, most of the catalysts traditionally used in the hydrosilation reaction of oxirane-containing olefins, particularly Pt-containing catalysts, promoted the oxirane ring-opening polymerization reaction, and therefore did not permit the selective preparation of oxirane-containing organosilicon compositions by the hydrosilation route.

It is therefore desirable to provide an efficient method for hydrosilation to prepare organosilicon compositions in the presence of a catalyst in amounts which do not promote the oxirane ring-opening polymerization of either the olefin or the organosilicon product. Such a method will provide a means for preparing an oxirane-containing organosilicon composition having a reproducible viscosity and longer shelf life.

The present invention relates to a method for preparing an organosilicon composition, said method comprising:
preparing a mixture comprising:
at least one olefin;
at least one silicon compound comprising silicon hydride groups, said olefin and said silicon compound being present in amounts such that the mixture comprises at least one reactive double bond per Si—H group;
a hydrosilation catalyst comprising at least one platinum (II) complex having the formula:
$PtL_2X_2$,
wherein each L is independently selected from the group consisting of $ER_3$, $E(OR)_3$, and $E(NR_2)_3$; each E is independently selected from the group consisting of phosphorus, arsenic, and antimony; each R is independently a hydrocarbyl group; and each X is independently selected from the group consisting of chloride, bromide, and iodide; said hydrosilation catalyst being present in an amount corresponding to an amount of platinum, said amount of hydrosilation catalyst being such that the amount of platinum present in said mixture is in a range between about 1 part per billion to less than 1000 parts per billion relative to a total weight of a product organosilicon composition;
optionally at least one solvent; and
reacting the mixture in the presence of oxygen at a temperature in a range from about ambient temperature to about 300° C., to produce said product organosilicon composition.

In one aspect of the present invention, the amount of hydrosilation catalyst used is such that the amount of platinum present is equivalent to more than about 1 part per billion (ppb) platinum and less than 1000 ppb platinum, the amount of platinum in parts per billion being relative to the total weight of the product organosilicon composition.

In a further aspect, the present invention relates to organosilicon compositions prepared by the method of the invention. In one aspect the present invention relates to stable oxirane-containing organosilicon compositions prepared by the method of the present invention.

DETAILED DESCRIPTION

As used herein, elements of Groups of the Periodic Table are made in reference to the "Periodic Table of the Elements", as published in "Chemical and Engineering News", 63(5), 27, 1985, said Table being incorporated herein by reference. In this format, the Groups are numbered 1 to 18.

The present invention may be understood more readily by reference to the following detailed description of preferred embodiments of the invention and the examples included herein. In this specification and in the claims that follow, reference will be made to a number of terms, which are defined to have the following meanings.

The singular forms "a", "an" and "the" include plural referents unless the context clearly dictates otherwise.

As used herein, the term "olefin" refers to a compound incorporating a carbon-carbon double bond.

As used herein the term "epoxyolefin" refers to an olefin, which also comprises an oxirane ring. Thus, 4-vinyl cyclohexene oxide is both an olefin and an epoxyolefin.

As used herein the term "silicon compound comprising silicon hydride groups" refers to a silicon compound comprising at least one SiH group. An example of a "silicon compound comprising hydride groups" is trimethylsilane ($Me_3SiH$). Triphenylsilane is also an example of a "silicon compound comprising SiH groups" as is tetramethydisilane (($HSiMe_2)_2$).

The term "silicon hydride" when used to describe a complete chemical compound has the same meaning as the term "silicon compound comprising silicon hydride groups". The term "silicon hydride group" refers to the SiH moiety present in a "silicon compound comprising silicon hydride groups". For example, trimethylsilane ($Me_3SiH$) is a "silicon hydride" which contains a "silicon hydride group", meaning that it contains an SiH moiety.

As used herein, the term "product organosilicon composition" refers to the product formed in a hydrosilation reaction between at least one "silicon compound comprising silicon hydride groups" as defined herein, and at least one "olefin" as defined herein.

The term "hydrocarbyl group", as used herein, denotes a monovalent, linear, branched, cyclic, or polycyclic group, which contains carbon and hydrogen atoms. The hydrocarbyl group may optionally contain atoms in addition to carbon and hydrogen selected from Groups 15, and 16 of the Periodic Table. Examples of monovalent hydrocarbyl groups include the following: $C_1$–$C_{30}$ alkyl; $C_1$–$C_{30}$ alkyl substituted with one or more groups selected from $C_1$–$C_{30}$ alkyl, $C_3$–$C_{15}$ cycloalkyl or aryl; $C_3$–$C_{15}$ cycloalkyl; $C_3$–$C_{15}$ cycloalkyl substituted with one or more groups selected from $C_1$–$C_{20}$ alkyl, $C_3$–$C_{15}$ cycloalkyl or aryl; $C_6$–$C_{15}$ aryl; and $C_6$–$C_{15}$ aryl substituted with one or more groups selected from $C_1$–$C_{30}$ alkyl, $C_3$–$C_{15}$ cycloalkyl or aryl group; where aryl preferably denotes a substituted or unsubstituted phenyl, naphthyl, or anthracenyl group.

The present invention is based upon the unexpected discovery that less than parts per million (ppm) levels of platinum, in the form of platinum(II) complexes comprising organophosphorus, organoarsenic, or organoantimony ligands, effectively catalyze the hydrosilation of an olefin with a silicon hydride to prepare an organosilicon composition. The use of such low levels of platinum catalyst in hydrosilation chemistry is unprecedented. For example, the prior art teaches that catalyst levels in excess of 1 part per million (ppm) of should be employed. The problem with known preparations of oxirane-containing organosilicon compositions is that the hydrosilation catalysts employed also catalyze the undesired polymerization of oxirane groups in either the oxirane-containing olefin starting material, the oxirane-containing organosilicon product, or both, which may lead to gel formation. Addition of, for example, high boiling amines inhibits gel formation, but also inhibits the hydrosilation reaction itself, thereby leading to incomplete conversion of reactants to products. To overcome the inhibitory effect of the stabilizer, higher loadings of the platinum (II) catalyst is required, which greatly increases the process cost, increases the reaction time, and discolors the product.

As stated previously, the method of the present invention provides an efficient and highly selective method for preparing an organosilicon composition under conditions which promote hydrosilation of an olefin with a silicon hydride to produce an organosilicon composition. Where the olefinic compound comprises an oxirane, under the conditions of the present invention, the oxirane rings of the starting material and the product oxirane-containing organosilicon composition remain substantially intact. By "substantially intact" it is meant that the level of oxirane ring opening, if any, does not produce a measurable effect on the viscosity of the product oxirane-containing organosilicon composition. Typically, this means that greater than 95 percent, more preferably more than 98 percent, and even more preferably more than 99 percent of the oxirane rings present in the starting material and product remain intact during the hydrosilation reaction.

The silicon hydride can be any type of a silicon compound having at least one Si—H group. There is no restriction on the range of functionality that can be present in the silicon hydride, so long as the functionality is inert under the hydrosilation reaction conditions. Examples of such inert functionality include hydrocarbyl, alkoxy, and aryloxy groups. Examples of silicon hydrides include tetramethyldisiloxane, triethoxysilane, methyldimethoxysilane, triethylsilane, methyldiethoxysilane, and the like. The silicon hydride can be a silane, a siloxane, or mixtures thereof. For the purposes of describing the present invention, a silane is defined as a compound having at least one hydride group and no Si—O—Si linkage, and a siloxane is defined as a compound having at least one hydride group and at least one Si—O—Si linkage. Both linear and branched structural variations of the silicon hydrides are included within the scope of the present invention. Besides linear and branched structures, the siloxanes may also comprise cyclic structures. Suitable examples of cyclic siloxanes having at least one hydride group include 1,3,5-trimethylcyclotrisiloxane, 1,3,5,7-tetramethylcyclotetrasiloxane, 1,3,5,7,9-pentamethylcyclopentasiloxane, and the like. Examples of linear organohydrogensiloxanes include 1,1,3,3-tetramethyldisiloxane, bis(dimethylsilyl)silicate, poly (dimethylsiloxane)-poly(methylhydrogensiloxane) copolymer, dialkylhydrogensilyloxy-endstopped polydialkylsiloxane, copolymer containing at least three alkylhydrogensilyloxy groups, (e.g., $(CH_3)_2(H)SiO[(CH_3)_2SiO]_x[(CH_3)(H)SiO]_ySi(H)(CH_3)_2$, where "x" and "y" are greater than or equal to 1), and the like. A mixture comprising cyclic and linear silicon hydrides may also be used as the hydrosilation reagent, thus leading to a rich diversity of hydrosilylated products.

The hydrosilation catalyst is a platinum(I) complex having the formula, $PtL_2X_2$, wherein each L is independently selected from the group consisting of $ER_3$, $E(OR)_3$, and $E(NR_2)_3$; each E is independently selected from the group consisting of phosphorus, arsenic, and antimony; each R is independently a hydrocarbyl group; and each X is independently selected from the group consisting of chloride, bromide, and iodide. Suitable examples of "L" include, but are not limited to, trimethylphosphine, triethylphosphine, tritolylphosphine, triphenylphosphine, triphenylstibine, triphenylarsine, tri-n-butylphosphine, tri-n-butylstibine, tri-n-butylarsine, trimethylphosphine, diphenylmethylphosphine, dimethylphosphine, trimethylphosphite, triethylphosphite, tri-n-butylphosphite, triphenylphosphite, tritolylphosphite, and the like.

Suitable examples of platinum(II) complexes include, but are not limited to, dichlorobis(triphenylphosphine)platinum, dibromobis(triphenylphosphine)platinum, diiodobis(triphenylphosphine)platinum, dichlorobis(triphenylstibine)platinum, dibromobis(triphenylstibine)platinum, diiodobis(triphenylstibine)platinum, dichlorobis(triphenylarsine)platinum, dibromobis(triphenylarsine)platinum, diiodobis(triphenylarsine)platinum dichlorobis(tri-n-butylphosphine)platinum, dibromobis(tri-n-butylphosphine)platinum, dichlorobis(trimethylphosphine)platinum, dichlorobis(triethylphosphine)platinum, dichlorobis(tritolylphosphine)platinum and the like. Catalyst compositions resulting from various combinations of "L" and "X", as will be apparent to those skilled in the art, will also function satisfactorily in the hydrosilation reaction according to the method of the present invention.

The hydrosilation catalyst described above can be introduced into the hydrosilation reaction mixture either as a pre-formed complex, or prepared in situ. In one embodiment of the preparation of the hydrosilation catalyst in situ, a platinum compound, $PtX_2$, wherein each "X" is independently selected from the group consisting of chloride, bromide, or iodide; is combined in the presence of the olefin and optionally the silicon compound containing Si—H groups, with a compound "L" having the formula, $ER_3$, $E(OR)_3$, or $E(NR_2)_3$, wherein E is selected from the group consisting of phosphorus, arsenic, and antimony; and each R is independently a hydrocarbyl group.

It has been unexpectedly discovered that ppb levels of the catalyst affords clean hydrosilation reaction products. The hydrosilation catalyst is present in an amount corresponding to an amount of platinum, said amount of hydrosilation catalyst being such that the amount of platinum present in said mixture is in a range between about 1 part per billion to less than 1000 parts per billion relative to the weight of the hydrosilation product. In a preferred embodiment, the amount of platinum present, as defined above, is from about 10 ppb to about 500 ppb relative to the weight of the hydrosilation product. In further preferred embodiment, the amount of platinum present, as defined above, is from about 50 ppb to about 200 ppb relative to the weight of the hydrosilation product.

The hydrosilation reaction can be carried out over a wide range of temperature. Although the invention is not limited by any theory of operation, it is believed that the temperature plays a crucial role in the activation of the platinum(II) complex catalyst through a process involving dissociation of the ligand L coordinated to the platinum center, thereby creating a coordinatively unsaturated site to interact with the olefin or the oxirane-containing olefin. The strength of the Pt(II)—L coordination bond in turn depends not only on the nature of E, but also on the nature of the "R", "OR", or "$NR_2$"-groups bonded to "E". The hydrosilation reaction can be carried out at any temperature from about ambient temperature to about 300° C. In a preferred embodiment, the reaction can be carried out from about ambient temperature to about 200° C.; while in a further preferred embodiment, the reaction can be carried out from about 50° C. to about 150° C.

A solvent may optionally be employed in the hydrosilation reaction. The use of a solvent is helpful when the silicon compound, the olefin, or both are solids or very viscous liquids, or when the reaction mixture thickens with time, whereby efficient stirring of the reaction mixture would be problematic. The use of a solvent may also aid in controlling the temperature of the reaction mixture. Suitable solvents that may be used according to the method of the present invention typically are those solvents having a boiling point from about 30° C. to about 250° C. In a preferred embodiment, the solvent has a boiling point from about 100° C. to about 200° C., and in a further preferred embodiment, the solvent has a boiling point from about 100° C. to about 160° C.

Suitable solvents for the hydrosilation reaction include those selected from the group consisting of $C_5$–$C_{30}$ substituted and unsubstituted aryl, aralkyl, and alkaryl hydrocarbons; linear and branched paraffins; and mixtures comprising any combination of the foregoing solvents. Examples of aromatic solvents include benzene, toluene, the individual xylene (ortho, meta, or para), and mixed isomeric xylenes, mesitylene, ethylbenzene, isopropylbenzene, (n-butyl)benzene, and the like. Examples of substituted aromatic solvents include those having alkoxy groups, such as anisole, alkylated anisoles, etc. Examples of linear and branched paraffin solvents include pentane, hexane, heptane, octane, isooctane, and other higher boiling commercially available paraffin mixtures. In particular embodiments, the solvent for the hydrosilation reaction is selected from the group consisting of toluene, the individual xylene (ortho, meta, or para), mixed isomeric xylenes, or mixtures comprising any combination of the foregoing solvents. In another particular embodiment, the solvent can be the silicon hydride groups.

The presence of oxygen is desirable for carrying out the hydrosilation reaction. In one embodiment, the reaction can be carried out under an ambient atmosphere. By ambient atmosphere it is meant that the reaction mixture is exposed to the atmosphere during the hydrosilation reaction.

The olefin component of the hydrosilation reaction can, in general, be any ethylenically unsaturated compound. Ethylenically unsaturated compounds are defined herein as compounds that possess at least one carbon-carbon double bond. The olefin may be substituted or unsubstituted. By substituted it is meant that the olefin comprises substituents other than hydrogen. Examples of substituents that may be present in substituted olefins include halogen atoms, alkyl groups, alkoxycarbonyl groups, alkoxy groups, and the like. Typically it is preferred that substituents present in the olefin starting material be inert under the hydrosilation reaction conditions. The olefinic compound may also contain an oxirane. Oxirane-containing olefins are valuable raw materials for the synthesis of oxirane-containing organosilicon compounds. The oxirane-containing olefin can generally be any type of an organic oxirane compound having one or more carbon-carbon double bonds anywhere in the molecule. Examples of suitable oxirane-containing olefins include, but are not limited to, allyl glycidyl ether, methallyl glycidyl ether, 1-methyl-4-isopropenyl cyclohexene oxide, 2,6-dimethyl-2,3-epoxy-7-octene, 1,4-dimethyl-4-vinylcyclohexene oxide, 4-vinylcyclohexene oxide, vinylnorbornene monoxide, dicyclopentadiene monoxide, 1,2-epoxy-6-heptene, and 1,2-epoxy-3-butene, and the like.

The amount of olefin necessary to carry out the hydrosilation reaction is generally such that the reaction mixture comprises at least one reactive double bond per Si—H group. The term "reactive double bond" is defined herein as a double bond that undergoes hydrosilation reaction with Si—H groups under the conditions of the present invention. Examples of reactive double bonds include the vinyl group of 4-vinyl cyclohexene oxide and the aliphatic double bond present in eugenol.

In a particular embodiment of preparing the organosilicon composition, the optional solvent, the olefin, and the platinum catalyst are mixed together prior to addition of the silicon hydride. The method described above is particularly useful for preparing an oxirane-containing organosilicon composition.

In another embodiment, the method of the present invention may be used to prepare an oxirane-containing organosilicon composition having a total weight after a final evaporation step, referred to here as Step (E), in which volatile components of the reaction mixture are removed after completion of the hydrosilation reaction. Such an embodiment comprises: (A) preparing a mixture by combining: i) at least one olefinic compound containing at least one oxirane ring, ii) optionally at least one solvent, iii) at least one hydrosilation catalyst comprising a platinum (II) complex having the formula $PtL_2X_2$, wherein each "L" is independently selected from the group consisting of $ER_3$, $E(OR)_3$, and $E(NR_2)_3$; each "E" is independently selected from the group consisting of phosphorus, arsenic, and antimony; each R is independently a hydrocarbyl group; and each "X" is independently selected from the group consisting of chloride, bromide, and iodide; said hydrosilation catalyst being present in an amount corresponding to an amount of platinum, said amount of hydrosilation catalyst being such that the amount of platinum present in said mixture is in a range between about 1 part and less than 1000 parts per billion relative to the total weight of the oxirane-containing organosilicon composition after the evaporation step (E); (B) heating the mixture formed in step (A) to a temperature from about 50° C. to about 250° C. in the presence of oxygen, (C) adding to the heated mixture at least one silicon hydride; (D) heating the mixture formed in steps (A)–(C) to a temperature between about 50° C. and about 300° C. until essentially all of the hydride groups have reacted; (E) an evaporation step comprising heating the mixture formed in steps (A)–(D) under reduced pressure to remove essentially all volatile material to furnish a oxirane-containing organosilicon composition, said oxirane-containing organosilicon composition comprising at least one oxirane ring; and wherein during steps (A)–(E), the oxirane rings either originally present in the olefinic compound or in the oxirane-containing organosilicon composition remain substantially intact. The phrase, "essentially all of the hydride groups have reacted" is meant to indicate complete consumption of all silicon hydride groups as determined by an analytical method. An example of an analytical method for this purpose is infrared spectroscopy.

The progress of the hydrosilation reaction may be followed by infrared spectroscopy by monitoring the disappearance of the Si—H absorption (which occurs at about 2100 $cm^{-1}$) of the silicon hydride. When the hydrosilation reaction is judged to be essentially complete, the volatile components, including the at least one solvent, if used, and any excess of the at least one olefin are evaporated under vacuum to afford the desired organosilicon composition. Typically, the product organosilicon compositions prepared by the method of the present invention are essentially colorless materials.

In a particular embodiment, a method for preparing an oxirane-containing organosilicon composition having a total weight after an evaporation step (E) comprises the steps of: (A) preparing in the presence of oxygen a mixture by combining: i) at least one solvent selected from the group consisting of toluene, xylenes, mesitylene and mixtures thereof, ii) 4-vinylcyclohexene oxide, the 4-vinylcyclohexene oxide being present in the mixture in an amount corresponding to a number of moles of 4-vinylcyclohexene oxide; and iii) a hydrosilation catalyst comprising the formula, $(PPh_3)_2PtX_2$, wherein each "X" is independently selected from the group consisting of chloride, bromide, and iodide, where the hydrosilation catalyst is present in an amount corresponding to an amount of platinum, where the amount of hydrosilation catalyst is such that the amount of platinum present in said mixture is in a range between about 1 part and less than 1000 parts per billion relative to the total weight of the oxirane-containing organosilicon composition after the evaporation step (E); (B) heating the mixture formed in step (A) to a temperature from about 110° C. to about 150° C.; (C) adding to the mixture formed in steps (A)–(B) at least one silicon hydride, where the silicon compound(s) is(are) added in an amount corresponding to between about 0.1 mole and about 1 mole of total Si—H group per mole of said 4-vinylcyclohexene oxide present in the mixture; (D) heating the mixture formed in steps (A)–(C) to a temperature between about 50° C. and about 300° C. until essentially all of the hydride groups have reacted; and (E) an evaporation step comprising heating the mixture formed in steps (A)–(D) under reduced pressure to remove essentially all volatile material to furnish an oxirane-containing organosilicon composition, wherein the oxirane-containing organosilicon composition comprising at least one oxirane ring; and wherein during steps (A)–(E), the oxirane rings originally present in the 4-vinylcyclohexene oxide and in the oxirane-containing organosilicon composition remain substantially intact.

In yet another embodiment, the method of the present invention provides a curable composition prepared using the general procedure described above, where the composition has a weight, and where the composition comprises less than 1000 parts per billion of platinum relative to the weight of the curable composition.

In the shorthand notation of depicting organosilicon polymer structure:

M represents $(CH_3)_3SiO_{1/2}$;

$M^E$ represents 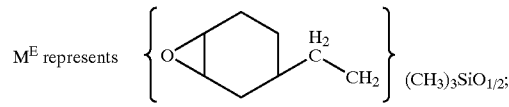 $(CH_3)_3SiO_{1/2}$;

$M^H$ represents $(CH_3)_2HSiO_{1/2}$;

D represents $(CH_3)_2Si(O_{1/2})_2$;

$D^E$ represents 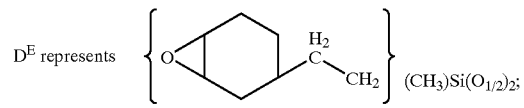 $(CH_3)Si(O_{1/2})_2$;

$D^H$ represents $(CH_3)HSi(O_{1/2})_2$; and

Q represents $Si(O_{1/2})_4$

The high selectivity of the hydrosilation reaction is utilized to prepare a variety of oxirane-containing organosilicon compositions, such as those represented by formulas (I) to (VI), as shown below, in high purity. These compositions are readily prepared from the corresponding silicon hydride compounds and vinylcyclohexene oxide (hereinafter sometimes referred to as "VCHO") as starting materials. The oxirane-containing organosilicon compositions are valuable monomers for preparing cured epoxy resins, which in turn are particularly valuable for preparing encapsulents for LED's.

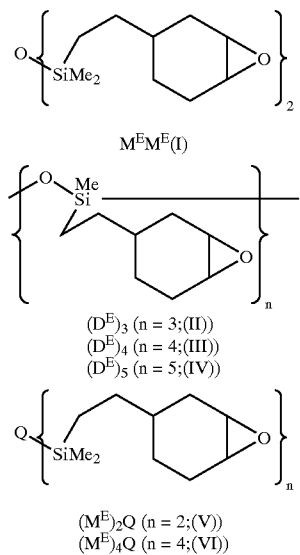

$M^EM^E$(I)

$(D^E)_3$ (n = 3;(II))
$(D^E)_4$ (n = 4;(III))
$(D^E)_5$ (n = 5;(IV))

$(M^E)_2Q$ (n = 2;(V))
$(M^E)_4Q$ (n = 4;(VI))

Using known hydrosilation conditions it is often difficult to prepare high quality, water-white materials. The primary issue is that the reaction must be very selective, afford a very high yield of the hydrosilylated product, and use such low levels of the hydrosilation catalyst that the catalyst can be left in the final organosilicon composition without affecting the shelf life of the organosilicon composition. The reason for this is that the product compositions have high boiling points and high viscosities, making it difficult or impossible to purify them. If such a reaction would avoid a purification step, some silicon compounds would become available in a high level of purity not possible by any other currently known method, as well as dramatically lowering the overall cost of the process. The process cost is lowered by use of much less of the expensive platinum-containing catalyst and elimination of a process for product purification. VCHO is a fairly reactive olefin substrate, readily hydrosilylated by various silicon compounds containing hydride groups. 1,1,3,3-Tetramethyldisiloxane ($M^HM^H$) is both reactive and volatile, thus making the preparation of (I) straightforward. Since many other high molecular weight polyfunctional oxirane-containing organosilicon compounds, such as the oxirane-containing organosiloxanes are non-volatile, viscous, and reactive liquids, their purification is practically limited to removal of volatile impurities by vacuum stripping. This results in oxirane-containing organosilicon compositions containing the platinum catalyst residue. Since the starting materials for the hydrosilation reaction are themselves relatively easily purified, one may obtain high quality oxirane-containing organosiloxanes if the hydrosilation is free of side reactions (vide infra) and essentially quantitative conversion is obtained.

The above method can be used for preparing a wide range of oxirane-containing organosilicon compounds, wherein a variety of silanes and siloxanes can be reacted with a variety of oxirane-containing olefins. Furthermore, the hydrosilafion reaction proceeds such that the oxirane rings in the oxirane-containing olefin and in the oxirane-containing organosilicon composition remain substantially intact throughout the course of the reaction and subsequent isolation of crude product. The method avoids the use of tertiary amine stabilizers to prevent the oxirane ring opening. The products are generally obtained as colorless materials, have good shelf life, and show no signs of viscosity increase, indicating that the oxirane ring in the product has not been polymerized.

In one embodiment, the compositions prepared using the methods disclosed herein are used in the manufacture of LED devices. In another embodiment, the present disclosure relates to the LED devices themselves which may be prepared using conventional LED manufacturing techniques which substitute the organosilicon compositions prepared according to the method of the present invention for conventional thermosetting materials. The compositions prepared according to the method of the present invention may be cured using conventional curing techniques to produce a cured composition. These curable compositions are valuable materials for preparing LED devices, and more particularly, the high luminosity LED devices. The curable compositions are used for producing new epoxy encapsulent materials having greater resistance to thermal aging while retaining the desirable properties of existing epoxy materials, such as resistance to crack propagation, ease of handling, high glass transition temperature, good adhesion, and low coefficient of thermal expansion.

The following examples are included to provide additional guidance to those skilled in the art in practicing the claimed disclosure. The examples provided are merely representative of the work that contributes to the teaching of the present application. Accordingly, these examples are not intended to limit the disclosure, as defined in the appended claims, in any manner.

EXAMPLES

Reactions were carried out under ambient atmosphere in clean but otherwise untreated glassware unless otherwise specified. 1,1,3,3-tetramethyldisiloxane ($M^HM^H$), 1,3,5-trimethylcyclotrisiloxane ($D^H_3$), 1,3,5 7-tetramethylcyclotetrasiloxane ($D^H_4$), 1,3,5,7,9-pentamethylcyclopentasiloxane ($D^H_5$), bis(dimethylsilyl) silicate, ($M^H_2Q$), and tetrakis(dimethylsiloxy)silane ($M^H_4Q$) were used as received from Gelest, Inc., or GE Silicones. VCHO was used as received from Aldrich. Solvents were reagent grade and used without further purification. Platinum and rhodium catalysts were used as received from Strem Chemical Company. Solutions of these catalysts were prepared using volumetric flasks in the following concentrations: 1.6 wt % $RhCl_3(SBu_2)_3$ in ethanol, 5 mg/ml $PtCl_2(SEt_2)_2$ in ethanol, and 5.1 mg/ml $PtCl_2(PPh_3)_2$ in dichloromethane, and stored in the dark. The term "millimoles" is represented by "mmol".

Comparative Example 1

This example describes the preparation of 1,3-bis(1,2-epoxy-4-cyclohexylethyl)-1,1,3,3-tetramethyldisiloxane, $M^EM^E$ (I) using $RhCl_3(SBu_2)_3$ as the hydrosilation catalyst.

This reaction was carried out under dry nitrogen, using hot glassware set-up. A 1-L, 3-necked, round-bottomed flask, equipped with a condenser, addition funnel, and thermometer was charged with 111 g (893 mmol) VCHO under nitrogen flow, followed by 14 microliters of $RhCl_3(SBu_2)_3$ catalyst solution (3 ppm Rh based on final product weight) and approximately 400 ml hexane. The addition funnel was charged with $M^HM^H$ (60 g, 447 mmol) under nitrogen, followed by 10 ml of hexane. The reaction mixture was heated to reflux with stirring, resulting in a solution temperature of 82° C. The silane was added dropwise over the course of an hour, resulting in an increase in reflux rate. The reaction was refluxed for two hours after complete addition of the $M^HM^H$, with periodic monitoring of the mixture by infrared spectroscopy. When the Si—H absorption of $M^HM^H$ at approximately 2100 cm$^{-1}$ disappeared, the reaction was judged to be complete. The solution was cooled to room temperature; the condenser and thermometer were replaced with stopcocks and the addition funnel with a short-path distillation head. The solution was stripped of volatile components until the vapor temperature was above 50° C., and then began to decrease. The colorless material that remained in the reaction flask weighed 169 g, with manipulative losses accounting for the lost material.

Comparative Example 2

This example describes the attempted preparation of compound (I) using $PtCl_2(SEt_2)_2$ as the hydrosilation catalyst.

A 3-liter, 3-necked round-bottomed flask equipped with a condenser, addition funnel, and thermometer was charged with 420 g (3.38 mol) VCHO, followed by 120 microliters of $PtCl_2(SEt_2)_2$ catalyst solution (4.8 ppm Pt based on final product weight) and approximately 800 ml hexane. 225 g (1.68 mol) of $M^HM^H$ was charged into the addition funnel (in 3 portions during addition), followed by 20 ml hexane. The reaction solution was heated to reflux with stirring. A 20 ml portion of $M^HM^H$ was added, with little response of the reaction solution. An additional 100 microliters of the Pt solution was added, causing the reaction to begin. The remaining $M^HM^H$ was added over the course of two hours. The reaction was refluxed for three hours after MHM addition was complete, with periodic testing of the mixture by infrared. When the Si—H absorption peak at approximately 2100 $cm^{-1}$ disappeared, the reaction was judged to be complete. The solution was cooled to room temperature and transferred to a 2-liter flask. A short path distillation head was added and the mixture heated under vacuum. The reaction mixture gels before the vapor temperature reached 35° C.

Example 1

This example describes the preparation of 1,3-bis(1,2-epoxy-4-cyclohexylethyl-1,1,3,3-tetramethyldisiloxane, $M^EM^E$ (I) using parts per billion levels of the hydrosilation catalyst, $PtCl_2(PPh_3)_2$.

A 1-liter, 3-necked, round-bottomed flask equipped with a condenser, addition funnel, and thermometer was charged with VCHO (111 g, 893 mmol), followed by 4 microliters of a solution of $PtCl_2(PPh_3)_2$ in dichloromethane (containing 150 ppb of Pt based on weight of final product) and toluene (150 ml). The addition funnel was charged with $M^HM^H$ (60 g, 447 mmol) under nitrogen, followed by toluene (10 ml). The reaction solution was heated to reflux with stirring, resulting in a solution temperature of 124° C. The $M^HM^H$ solution was then added drop wise over the course of about 45 min, resulting in an increase in reflux rate and solution temperature to 126° C. After the addition of the $M^HM^H$ solution was complete, the reaction mixture was refluxed for about four hours, with periodic testing of the reaction mixture by infrared spectroscopy. When the peak at approximately 2100 $cm^{-1}$ disappeared, indicating complete consumption of $M^HM^H$, the reaction was judged to be complete. The solution was cooled to room temperature; the condenser and thermometer were replaced with stopcocks and the addition funnel with a short-path distillation head. The solution was heated with a water bath at 85° C. and stripped of volatile components until the vapor temperature was above 70° C. No gel formation was observed during and after the stripping process. Proton NMR spectrum of the residual material in the reaction flask showed it to be the desired product and free of residual solvent and VCHO. The final product weighed 163.5 g. Manipulative losses account for the lost material.

Comparative Example 3

This example describes the attempted preparation of 1,3,5,7-tetrakis(1,2-epoxy-4-cyclohexylethyl)-1,3,5,7-tetramethylcyclotetra-siloxane, $D^E_4$, (represented by formula (E)) using $RhCl_3(SBu_2)_3$ as the hydrosilation catalyst.

This reaction was carried out under dry nitrogen, using hot glassware set-up. A 250 ml 3-necked round-bottomed flask, equipped with a condenser, addition funnel, and thermometer was charged with VCHO (30 g, 242 mmol) under nitrogen flow, followed by 3 microliters of $RhCl_3(SBu_2)_3$ catalyst solution (containing 1 ppm Rh based on final product weight) and approximately 50 ml hexane. The addition funnel was charged with $D^H_4$ (12.9 g, 53.7 mmol) under nitrogen, followed by hexane (10 ml). The reaction solution was heated to reflux with stirring. One third of the $D^H_4$ solution was added drop wise, with no obvious result (e.g., onset of a reflux and/or a rise in reaction mixture temperature), and the reaction refluxed 30 min. The mixture was tested by infrared, showing a large Si—H peak. An additional 3 microliters of the rhodium catalyst solution (equivalent to 1 ppm more of Rh based on final product weight) was added, but there was still no reaction. One half of the remaining $D^H_4$ solution and an additional 3 microliters of catalyst solution (equivalent to 1 ppm more of Rh based on final product weight) were added, followed by continued reflux. A check of the reaction by IR showed a very large Si—H peak indicating a large amount of unreacted $D^H_4$. The hexane was stripped off at atmospheric pressure to give a concentrated reaction mixture, which was heated to reflux, resulting in a solution temperature of 128.5° C. The remaining $D^H_4$/hexane solution was then added, causing the reaction temperature to drop to 105° C. After refluxing for about 3 hours, IR spectroscopic analysis showed that some unreacted $D^H_4$ was still present. To this mixture was added 6 microliters more of the catalyst solution (equivalent to 2 ppm more of Rh based on final product weight), followed by refluxing to 95° C. This led to an increase in viscosity of the reaction mixture, however unreacted $D^H_4$ was still present, as shown by IR spectral analysis. Cooling the reaction mixture to room temperature afforded a liquid whose viscosity was visually much higher than expected.

Comparative Example 4

This example describes the attempted preparation of 1,3,5,7-tetrakis(1,2-epoxy-4-cyclohexylethyl)-1,3,5,7-tetramethylcyclotetra-siloxane, $D^E_4$, (represented by formula (III)) using $PtCl_2(SEt_2)_2$ as the hydrosilation catalyst.

A 250 ml 3-necked round-bottomed flask, equipped with a condenser, addition funnel, and thermometer was charged with VCHO (30 g, 242 mmol) followed by 3 microliters of $PtCl_2(SEt2)_2$ catalyst solution (375 ppb Pt based on final product weight), 4 microliters of tridodecylamine, and 50 ml toluene. The reaction solution was heated to reflux with stirring. To this mixture was added 6.5 g (27.1 mmol) $D^H_4$ (1,3,5,7-tetramethylcyclotetramethylsiloxane) was added drop wise via a syringe. After addition of the $D^H_4$ reactant, the resulting mixture was refluxed for 90 min. The IR spectrum of an aliquot of the reaction mixture indicated the presence of some unreacted $D^H_4$ silane. An additional 3 microliters of the above platinum catalyst solution (equivalent to 375 ppb more of Pt based on final product weight) was added, and the reaction mixture was refluxed for an additional 30 min. The reaction mixture was cooled to room temperature and stripped under vacuum. The residual material remaining in the flask was a thick, yellow-green oil.

Example 2

This example describes the preparation of 1,3,5,7-tetrakis(1,2-epoxy-4-cyclohexylethyl)-1,3,5,7-tetramethylcycloteta-siloxane, $D^E_4$, (represented by formula (III) using parts per billion levels of $PtCl_2(PPh_3)_2$ as the hydrosilation catalyst.

A 1-liter, 3-necked round-bottomed flask equipped with two condensers and a thermometer was charged with VCHO (122 g, 981 mmol), 49 g (204 mmol) $D^H_4$ (1,3,5,7-tetramethylcyclotetrasiloxane), 4 microliters of $PtCl_2(PPh_3)_2$ catalyst solution (140 ppb Pt based on final product weight) and 83 g toluene. The reaction solution was heated to reflux with stirring, resulting in a solution temperature of 123° C. At this point the reaction mixture began to reflux vigorously, with the solution temperature reaching 135° C. initially, and thereafter settling down at 130° C. The mixture was then refluxed for about 3 hours. At this point, the infrared spectrum of an aliquot of the reaction mixture showed no Si—H absorption indicating complete consumption of $D^H_4$ The solution was cooled to room temperature, and the condensers and thermometer were replaced with stopcocks and a short-path distillation head. The solution was heated with a water bath at 85° C. and stripped of volatile components until the vapor temperature was above 70° C. No gel formation was observed during and after the stripping process. Proton NMR spectrum of the residual material in the reaction flask showed it to be the desired product and free of residual solvent and VCHO. In this manner, 148 g of (III) was obtained as a colorless material.

Example 3

This example describes the preparation of tetrakis(1,2-epoxy-4-cyclohexylethyl dimethylsiloxy)silane, $M^E_4Q$ (represented by formula (VI)) using parts per billion levels of $PtCl_2(PPh_3)_2$ as the hydrosilation catalyst.

A 1 liter, 3-necked round-bottomed flask equipped with two condensers and a thermometer was charged with VCHO (121.3 g, 977 mmol), 66.1 g (201 mmol) of $M^H_4Q$ (tetrakis(dimethylsilyloxy)silane), 4.4 microliters of $PtCl_2(PPh_3)$ catalyst solution (140 ppb Pt based on final product weight), and 80 g toluene. The reaction solution was heated to reflux with stirring, resulting in a solution temperature of 129° C. At this point the reaction mixture began to reflux vigorously, with the solution temperature reaching 140° C. initially, and then settling down to 132° C. The mixture was then refluxed for 3 hours. At this point, the infrared spectrum of an aliquot of the reaction mixture showed no Si—H absorption indicating complete consumption of $M^H_4Q$. The solution was cooled to room temperature, and the condensers and thermometer were replaced with stopcocks and a short-path distillation head. The solution was heated with a water bath at 85° C. and stripped of volatile components until the vapor temperature remained above 50° C. for about 30 min. No gel formation was observed during and after the stripping process. Proton NMR spectrum of the residual material in the reaction flask showed it to be the desired product and free of residual solvent and VCHO. In this manner, 160 g of (VI) was obtained as a colorless material.

TABLE 1

Summarized Results of Examples 1–3 and Comparative Examples 1–4.

| Example Number | VCHO (grams) | Silicon hydride (grams) | Hydrosilation catalyst (ppb) | Product (grams) | Physical properties of isolated product |
|---|---|---|---|---|---|
| 1 | 111 | $M^HM^H$ (60) | $PtCl_2(PPh_3)_2$ (150) | 163.5 | Colorless material; no gelling |
| 2 | 122 | $D^H_4$ (49) | $PtCl_2(PPh_3)_2$ (140) | 148 | Colorless material; no gelling |
| 3 | 121.3 | $M^H_4Q$ (66.1) | $PtCl_2(PPh_3)_2$ (140) | 160 | Colorless material; no gelling |
| 1* | 111 | $M^HM^H$ (60) | $RhCl_3(SBu_2)_3$ (3000) | 169 | Colorless material; no gelling |
| 2* | 420 | $M^HM^H$ (225) | $PtCl_2(SEt_2)_2$ (8800) | NM | Extensively gelled material |
| 3* | 32 | $D^H_4$ (12.9) | $RhCl_3(SBu_2)_3$ (3000) | NM | Extensively gelled material |
| 4* | 30 | $D^H_4$ (12.9) | $PtCl_2(SEt_2)_2$ (750) | NM | Green, extensively gelled material |

*Indicates a Comparative Example. "NM" indicates "Not Measurable". "ppb" refers to parts per billion catalyst.

The results obtained in the above Examples are summarized in Table 1 below. Examples 1–3 demonstrate that organosilicon compositions without any gel formation may be prepared according to the method of the present invention using less than 10 percent of the catalyst employed in conventional methods of preparing organosilicon compositions.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method for preparing an organosilicon composition, said method comprising preparing a mixture comprising:
   at least one epoxyolefin;
   at least one silicon compound containing silicon hydride (Si—H) groups, said epoxyolefin and said silicon compound being present in an amount such that the mixture comprises at least one reactive double bond per Si—H group;

a hydrosilation catalyst comprising at least one platinum (II) complex having the formula

$PtL_2X_2$, wherein each L is independently selected from the group consisting of $ER_3$, $B(OR)_3$, and $E(NR_2)_3$; each E is independently selected from the group consisting of phosphorus, arsenic, and antimony, each R is independently a hydrocarbyl group; and each X is independently selected from the group consisting of chloride, bromide, and iodide; said hydrosilation catalyst being present in an amount corresponding to an amount of platinum, said amount of hydrosilation catalyst being such that the amount of platinum present in said mixture is in a range between about 1 part per billion to less than 1000 parts per billion relative to a total weight of a product organosilicon composition;

optionally at least one solvent; and reacting the mixture in the presence of oxygen at a temperature in a range from about 110 to about 300° C. to produce said product organosilicon composition.

2. The method of claim 1, wherein the catalyst is present in an amount corresponding to between about 10 parts to about 300 parts platinum per billion parts of the product organosilicon composition.

3. The method of claim 1, wherein the catalyst is present in an amount corresponding to between about 50 parts to about 200 parts platinum per billion parts of the product organosilicon composition.

4. The method of claim 1, wherein said reacting the mixture is carried out at a temperature from about 110 to about 200° C.

5. The method of claim 1, wherein said reacting the mixture is carried out at a temperature from about 110 to about 150° C.

6. The method of claim 1, wherein said at least one solvent is selected from the group consisting of $C_5$–$C_{30}$ substituted and unsubstituted aryl, aralkyl, and alkaryl compounds; linear and branched paraffins, silanes and siloxanes comprising at least one silicon atom.

7. The method of claim 1, wherein each L is independently selected from the group consisting of triphenylphosphine, triphenylstibine, triphenylarsine, tri-n-butylphosphine, tri-n-butylstibine, tri-n-butylarsine, trimethylphosphine, triethylphosphine, trioctylphosphine, diphenylmethylphosphine, dimethylphosphine, trimethylphosphite, triethylphosphite, tri-n-butylphosphite, triphenylphosphite, tritolylphosphite, tritolylphosphine, and mixtures thereof.

8. The method of claim 1, wherein said platinum (II) complex is selected from the group consisting of dichlorobis(triphenylphosphine)platinum, dibromobis(triphenylphosphine)platinum, diiodobis(triphenylphosphine)platinum, dichlorobis(triphenylstibine)platinum, dibromobis(triphenylstibine)platinum, diiodobis(triphenylstibine)platinum, dichlorobis(triphenylarsine)platinum, dibromobis(triphenylarsine)platinum, diiodobis(triphenylarsine)platinum dichlorobis(tri-n-butylphosphine)platinum, dibromobis(tri-n-butylphosphine)platinum, dichlorobis(trimethylphosphine)platinum, dichlorobis(tritolylphosphine)platinum dichlorobis(trioctylphosphine)platinum, and mixtures thereof.

9. The method of claim 1, wherein said at least one epoxyolefin is selected from the group consisting of allyl glycidyl other, methallyl glycidyl ether, 1-methyl-4-isopropenyl cyclohexene oxide, 2,6-dimethyl-2,3epoxy-7-octene, 1,4-dimethyl-4-vinylcyclohexene oxide, 4-vinylcyclohexene oxide, vinylnorbornene monoxide, dicyclopentadiene monoxide, 1,2-epoxy-6-heptene, and 1,2-epoxy-3-butene.

10. The method of claim 1, wherein said mixture is prepared by first combining said a least one solvent, said at least one epoxyolefin, and said catalyst in a first step and then subsequently adding said at least one silicon compound containing silicon hydride groups.

11. The method of claim 1, wherein said at least one silicon compound containing silicon hydride groups is selected from the group consisting of linear, branched and cyclic organohydrogensiloxanes.

12. The method of claim 1, wherein said at least one silicon compound containing hydride groups is selected from the group consisting of 1,1,3,3-tetramethyldisiloxane, 1,3,5-trimethylcyclotrisiloxane, 1,3,5,7-tetramethylcyclotetrasiloxane, 1,3,5,7,9-pentamethylcyclopentasiloxane, bis(dimethylsilyl)silicate, and poly(dimethylsiloxanepoly(methylhydrogensiloxane) copolymer.

13. The method of claim 1, wherein said at least one solvent has a boiling point from about 50° C. to about 250° C.

14. The method of claim 1, wherein said at least one solvent has a boiling point from about 100° C. to about 160° C.

15. The method of claim 1, wherein said reacting the mixture in the presence of oxygen is carried out under an ambient atmosphere.

16. The method of claim 1, wherein the hydrosilation catalyst is prepared in situ.

17. A method according to claim 16 wherein said hydrosilation catalyst is pried by a method comprising adding to a mixture comprising said epoxyolefin, at least one compound having the formula PtX2, wherein each X is independently selected from the group consisting of chloride, bromide, or iodide; and adding at least one compound L independently selected from the group consisting of $ER_3$, $E(OR)_3$, and $E(NR_2)_3$; wherein each E is independently select from the group consisting of phosphorus, arsenic, and antimony; and each R is independently a hydrocarbyl group.

18. A method for preparing an oxirane-containing organosilicon composition, said oxirane-containing organosilicon composition having a total weight after an evaporation step (E), said method comprising the steps of:

Step (A) preparing in the presence of oxygen a mixture by combining:
i) at least one olefinic compound containing at least one oxirane ring,
ii) at least one solvent,
iii) at least one hydrosilation catalyst comprising at least one platinum (II) complex having the formula:

$PtL_2X_2$, wherein each L is independently selected from the group consisting of $ER_3$, $E(OR)_3$, and $E(NR)_3$; each B is independently selected from the group consisting of phosphorus, arsenic, and antimony each R is independently a hydrocarbyl group; and each X is independently selected from the group consisting of chloride, bromide, and iodide; said hydrosilation catalyst being present in an amount corresponding to an amount of platinum, said amount of hydrosilation catalyst being such that the amount of platinum present in said mixture is in a range between about 1 part per billion to less than 1000 parts per billion relative to the weight of the oxirane-containing organosilicon composition after the evaporation step (E);

Step (B) heating the mixture formed in step (A) to a temperature from about 110° C. to about 250° C.;

Step (C) adding to the mixture formed in steps (A)–(B) at least one silicon compound containing silicon hydride (Si—H) groups; said at least one silicon compound being added in an amount corresponding to between about 0.1 mole and about 1 mole of Si—H group per mole of said at least one olefinic compound containing at least one oxirane ring present in the mixture;

Step (D) heating the mixture formed in steps (A)–(C) to a temperature between about (110° C. and about 300° C. until essentially all of the hydride groups have reacted;

Step (E) an evaporation step comprising heating the mixture formed in steps (A)–(D) under reduced pressure to remove essentially all volatile material to furnish an oxirane-containing organosilicon composition, said oxirane containing organosilicon composition comprising at least one oxirane ring; and wherein during steps (A)–(E), the oxirane rings originally present in the olefinic compound containing at least one oxirane ring and in the oxirane-containing organosilicon composition remain substantially intact.

19. The method of claim 18, wherein said at least one silicon hydride is selected from the group consisting of 1,1,3,3-tetramethyldisiloxane, 1,3,5-trimethylcyclotrisiloxane, 1,3,5,7-tetramethylcyclotetrasiloxane, 1,3,5,7,9-pentamethylcyclopentasiloxane, and poly(dimethylsiloxane-poly(methylhydrogensiloxane) copolymers.

20. The method of claim 18, wherein at least one L is selected from the group consisting of triphenylphosphine, triphenylstibine, triphenylarsine, tri-n-butylphosphine, tri-n-butylstibine, tri-n-butylarsine, trimethylphosphine, triethylphosphine, tritolylphosphine, trioctylphosphine, diphenylmethylphosphine, dimethylphosphine, trimethylphosphite, triethylphosphite, tri-n-butylphosphite, triphenylphosphite and tritolylphosphite.

21. The method of claim 18, wherein said at least one hydrosilation catalyst is selected from the group consisting of dichlorobis(triphenylphosphine)platinum, dibromobis(triphenylphosphine)platinum, diiodobis(triphenylphosphine)platinum, dichlorobis(triphenylstibine)platinum, dibromobis(triphenylstibine)platinum, diiodobis(triphenylstibine)platinum, dichlorobis(triphenylarsine)platinum, dibromobis(triphenylarsine)platinum, diiodobis(triphenylarsine)platinum dichlorobis(tri-n-butylphosphine)platinum, dibromobis(tri-n-butylphosphine)platinum, dichlorobis(trimethylphosphine)platinum, dichlorobis(triethylphosphine)platinum, dichlorobis(trioctylphosphine)platinum, dichlorobis(tritolylphosphine)platinum.

22. The method of claim 18, wherein said at least one catalyst is present in an amount corresponding to from about 10 to about 500 parts per billion of platinum relative to the total weight of the oxirane-containing organosilicon composition after the evaporation step (E).

23. The method of claim 18, wherein said at least one catalyst is present in an amount corresponding to from about 50 to about 200 parts per billion of platinum relative to the total weight of the oxirane-containing organosilicon composition after the evaporation step (E).

24. A method for preparing an oxirane-containing organosilicon composition, said oxirane-containing organosilicon composition having a total weight after en evaporation step (E), said method composing the steps of:

Step (A) preparing in the presence of oxygen a mixture by combining:
  i) a solvent selected from the group consisting of toluene, isomeric xylenes, and mesitylene,
  ii) 4-vinylcyclohexene oxide, said 4-vinylcyclohexene oxide being present in the mixture in an amount corresponding to a number of moles of 4-vinylcyclohexene oxide, and
  iii) a hydrosilation catalyst comprising the formula, $(PPh_3)_2PtX_2$, wherein each X is independently selected from the group consisting of chloride, bromide, and iodide, said hydrosilation catalyst being present in an amount corresponding to an amount of platinum, said amount of hydrosilation catalyst being such that the amount of platinum present in said mixture is in a range between about 1 part and less than 1000 parts per billion relative to the total weight of the oxirane-containing organosilicon composition after the evaporation step (E);

Step (B) heating the mixture formed in step (A) to a temperature from about 110° C. to about 140° C.;

Step (C) adding to the mixture formed in steps (A)–(B) at least one silicon compound containing silicon hydride (Si—H) groups, said silicon compound being added in an amount corresponding to between about 0.1 mole and about 1 mole of Si—H group per mole of said 4-vinylcyclohexene oxide present in the mixture, Step (D) heating the mixture formed in steps (A)–(C) to a temperature between about 110° C. and about 300° C. until essentially all of the hydride groups have reacted;

Step (E) an evaporation step comprising heating the mixture formed in steps (A)–(D) under reduced pressure to remove essentially all volatile material to furnish an oxirane-containing organosilicon composition, said oxirane-containing organosilicon composition comprising at least one oxirane ring; and wherein during steps (A)–(E), the oxirane rings originally present in the 4-vinylcyclohexene oxide and in the oxirane-containing organosilicon composition remain substantially intact.

25. The method of claim 24, wherein the catalyst is present in an amount corresponding to from about 10 to about 500 parts per billion of platinum relative to the total weight of the oxirane-containing organosilicon composition after the evaporation step (E).

26. The method of claim 24, wherein the catalyst is present in an amount corresponding to from about 50 to about 200 parts per billion of platinum relative to the total weight of the oxirane-containing organosilicon composition after the evaporation step (E).

27. A curable oxirane-containing organosilicon composition prepped by the method of claim 1, said composition having a weight, said composition comprising less than 1000 parts per billion platinum relative to the weight of the curable composition.

28. A light emitting diode comprising the cured composition of claim 27.

* * * * *